US009289152B2

(12) United States Patent
    Shaduri

(10) Patent No.: US 9,289,152 B2
(45) Date of Patent: Mar. 22, 2016

(54) DEVICE TO DETECT MALIGNANT PROCESSES IN LIVING ORGANISMS

(75) Inventor: Marina Shaduri, Tbilisi (GE)

(73) Assignee: Advanced Bioresearch and Technology, S.A., Luxembourg (LU)

(*) Notice: Subject to any disclaimer, the term of this patent is extended or adjusted under 35 U.S.C. 154(b) by 565 days.

(21) Appl. No.: 12/531,465

(22) PCT Filed: Mar. 14, 2008

(86) PCT No.: PCT/GE2008/000003
    § 371 (c)(1),
    (2), (4) Date: Sep. 15, 2009

(87) PCT Pub. No.: WO2008/114065
    PCT Pub. Date: Sep. 25, 2008

(65) Prior Publication Data
    US 2010/0103252 A1    Apr. 29, 2010

(30) Foreign Application Priority Data
    Mar. 16, 2007    (GE) .................................... 009927

(51) Int. Cl.
    *H04N 7/18*    (2006.01)
    *A61B 5/05*    (2006.01)
    *A61B 5/00*    (2006.01)
(52) U.S. Cl.
    CPC ................. *A61B 5/05* (2013.01); *A61B 5/0059* (2013.01); *A61B 5/415* (2013.01); *A61B 5/418* (2013.01); *H04N 7/18* (2013.01)
(58) Field of Classification Search
    None
    See application file for complete search history.

(56) References Cited

U.S. PATENT DOCUMENTS 5,131,398 A    7/1992    Alfano et al.
6,002,786 A *  12/1999   Hallibert et al. .............. 382/124
                         (Continued)

FOREIGN PATENT DOCUMENTS

AU    754229    11/2002
DE    3340104    5/1985
                (Continued)

OTHER PUBLICATIONS

Korotkov. "Analysis of the Human Energy State with Gas Discharge Visualization Technique." *IEEE*. 2005. pp. 431-463.
(Continued)

*Primary Examiner* — Frederick Bailey
*Assistant Examiner* — Edemio Navas, Jr.
(74) *Attorney, Agent, or Firm* — Merchant & Gould P.C.

(57) ABSTRACT

The invention concerns a device for non-invasive detection of malignant processes in human body. Diagnostically informative optical data are obtained by exposing human fingertips to pulsed electric fields strong enough to initiate atmospheric pressure corona discharge. The device that provides reliable information useful for detection of cancer-specific spectral signatures comprises a transparent electrode (4) to generate electric impulses, which is covered by a rigid transparent insulator (3); a flexible transparent membrane (2) positioned loosely on the free surface of the rigid insulator to facilitate the recombination processes; a dark opaque membrane (1) positioned on the transparent membrane to eliminate spurious light; an image-receiving camera (5) mounted beneath the optically transparent electrode and a computer to operate the device and process recorded data. Proper arrangement of 3 dielectric layers and the recording of images when thermodynamic equilibrium is already established, significantly improves the reproducibility of optical data.

2 Claims, 3 Drawing Sheets

Schematic diagram of the gas-discharge device

(56) References Cited

U.S. PATENT DOCUMENTS

Figure 1:
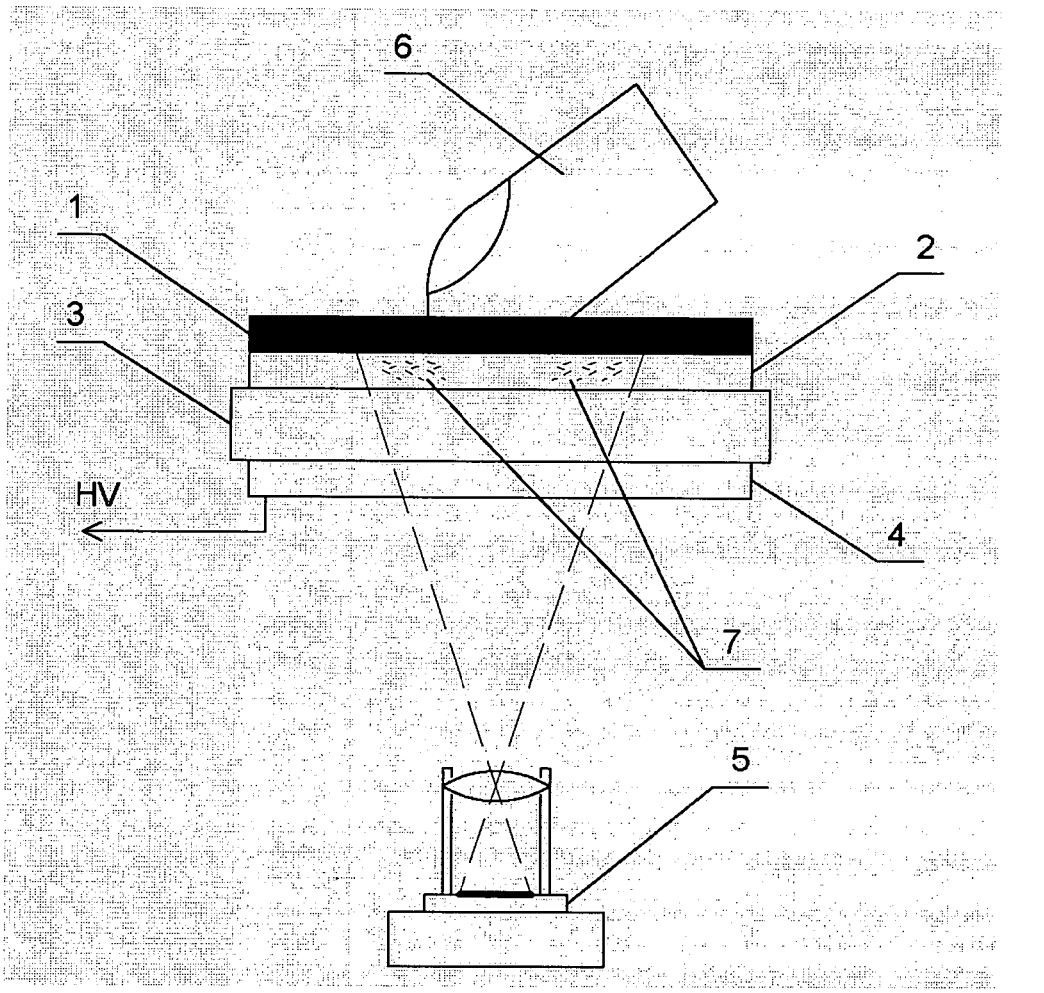

| | | | |
|---|---|---|---|
| 2002/0062074 A1* | 5/2002 | Zhdanov | 600/407 |
| 2002/0090650 A1* | 7/2002 | Empedocles et al. | 435/7.1 |
| 2003/0095316 A1* | 5/2003 | Herbepin et al. | 359/228 |
| 2005/0014998 A1 | 1/2005 | Korotkov | |
| 2005/0207487 A1* | 9/2005 | Monroe | 375/240.01 |
| 2006/0084845 A1* | 4/2006 | Korotkov | 600/300 |
| 2007/0178067 A1* | 8/2007 | Maier et al. | 424/93.2 |
| 2008/0312532 A1* | 12/2008 | Van Pieterson et al. | 600/431 |

FOREIGN PATENT DOCUMENTS

| | | |
|---|---|---|
| GE | P 2000 2225 | 6/2000 |
| RU | 2072791 | 2/1997 |
| RU | 2110824 | 10/1998 |
| RU | 2 211 659 | 9/2003 |
| RU | 2217047 | 11/2003 |
| SU | 442536 | 5/1975 |
| SU | 788468 | 3/1987 |
| WO | WO 99/27417 | 3/1999 |
| WO | WO 99/30612 | 6/1999 |
| WO | WO 00/75752 | 12/2000 |
| WO | WO 03/053240 | 3/2003 |
| WO | WO 2004/075752 | 10/2004 |

OTHER PUBLICATIONS

Shaduri. "Secondary holodiffractional radiation of biological systems." *Kybernetes*. vol. 34. No. 5. 2005. pp. 666-680.

Popp et al. "Delayed luminescence of biological systems in terms of coherent states." *Physics Letters*. vol. 293. 2002. pp. 93-87.

Bundzen et al. "Altered States of Consciousness: Review of Experimental Data Obtained with at Multiple Techniques Approach." *J. of Alternative and Complementary Med*. vol. 8 No. 2. 2002 pp. 153-165.

Korotkov "Analysis and monitoring of the human energy . . . " http://ieeexplore.ieee.org/xpl/freeabs_all.jsp?arnumber=1467728.

Pashchenko et al. "Systems Laws and Regulations in Electrodynamics. Nature and Society: The Institute of Control Problems." ISBN 5020130885. (2001) English abstract submitted herewith.

Shaduri et al.: "Holo-Imaging": The Principle of Holography and Its Practical Application, Proceeding of the Int. Conf. Actual Problems of Modern Physics (2008), pp. 94-97.

Correspondence regarding "CID-system Pilot Study"; Dr. Bernard Filoche, Digestive Pathology Department of Saint Philibert Hospital in Lille (France), Sep. 20, 2011, with English translation (2 pages).

Correspondence regarding "Bioholotomography (BHT) test"; Dr. Frank Chikli, Centre Hospitalier de Cannes (France), Nov. 12, 2013 (1 page).

Shaduri et al.: "Life-Cycling of Cancer: New Concept"; Cancer Treatment—Conventional and Innovative Approaches, Prof. Leticia Rangel (Ed.), Chapter 24, May 9, 2013, ISBN 978-983-51-1098-9, pp. 583-618.

Shaduri: "The Holographic Principle and Emergence Phenomenon"; Computer and Information Science, Human-Computer Interaction, Holography, Research and Technologies, Joseph Rosen (Ed.) Feb. 28, 2011, ISBN 978-953-307227-2 pp. 27-55.

Correspondence regarding "BHT datapoint collection of participants with untreated early stage solid cancer for CID-System automated software validation"; Raewyn Idoine, Southern Health and Disability Ethics Committees, Sep. 10, 2015 (3 pages).

* cited by examiner

Schematic diagram of the gas-discharge device

External view of gas-discharge device

DEVICE TO DETECT MALIGNANT PROCESSES IN LIVING ORGANISMS

This application is a National Stage Application of PCT/GE2008/000003, filed 14 Mar. 2008, which claims benefit of Serial No. AP 2007 009927, filed 16 Mar. 2007 in Georgia and which applications are incorporated herein by reference. To the extent appropriate, a claim of priority is made to each of the above disclosed applications.

The invention relates to electronics and biomedicine and it can be used to evaluate some characteristics of dynamic systems, e.g. to detect (or exclude) malignant processes in organism via gas-discharge imaging of a body parts under certain fitted conditions and further computerized processing of the images so obtained.

A known device [RU 2110824, prior date Nov. 26, 1997. Gas discharge visualization device. MKI G03B41/00; International conventional application PCT/RU97/00376, application analog RU 2110824 and patents AU, BR. Gas discharge visualization device; WO/1999/030612 Method for determining the energy-information characteristics of a biological object; WO/2003/053240 Method for diagnosis of human organism; WO/2004/075752) Method for determining the anxiety level of a human being] comprises a transparent electrode for generating an electrical field, dielectric for insulating an object under examination, and a television camera both the dielectric and the electrode being made of an optically transparent material the electrode being positioned between the dielectric and the television camera.

The shortcoming of the said device is that some spurious light interferes with gas-discharge image of an object under examination, the light being reflected from the surface of the latter. Spurious light is superimposed on emission of the object resulting in poorer contrast of image that complicates further computer processing and decreases the reproducibility rate of results.

Another shortcoming is application of a television camera that fixes frames in an interlaced mode. In fact, the frames so obtained contain two halves of an interlaced field deteriorating quality of a rapidly altering gas-discharge image of the object under examination.

The gas-discharge glow, which takes place around objects in case they contact directly with the surface of rigid dielectric layer, is changing under the influence of numerous sometimes uncontrollable factors like ambient temperature or humidity, or object's variable pressing force on the electrode, etc. Also, some functional processes (e.g., psycho-emotional state, neuro-hormonal dysfunctions, perspiration and the like) influence the gas-discharge image in case human finger-tips are pressed to the free surface of rigid dielectric layer. It is not likely to be possible to extract most stable and diagnostically comprehensive components out of a "mixed" picture acquired in the above-described conditions.

Engineering Result of the Invention

The engineering result of the invention is in detecting an emission in the range of relatively high frequencies to evaluate the synchronicity of system processes in the said range via recording its superficial emission that might be also used for the detection of malignant processes in living systems. This result is achieved by way of clearing and contrasting gas-discharge images under conditions of discretely altered external electrical field as well as in improving image quality and its reproducibility rate while using some additional (transparent and nontransparent) layers of flexible dielectric membranes.

NATURE OF THE INVENTION

A device for gas-discharge imaging to detect those asynchronous processes that belong to the range of high frequencies and are characteristic for malignant processes in living organisms comprises an optically transparent electrode to generate an electric field, a dielectric and an image-receiving television camera wherein a dielectric being capable to be mounted on an optically transparent electrode comprises three successive layers, each one in contact with the adjacent one: a rigid transparent electrically-insulating layer, a flexible transparent membrane positioned on the free surface of the rigid one to improve the quality and stability of imaging results and a dark opaque flexible membrane positioned on the free surface of the flexible transparent membrane to absorb spurious light reflected from the surface of a body part. An image-receiving progressive-scan monochrome camera is mounted beneath the optically transparent electrode to form a continuous analog video signal to be sent to a computer for further processing. This camera can be optionally replaced with a digital photographic camera.

The gas-discharge device comprises a dielectric being capable to be mounted on an optically transparent electrode (4), which in turn is a part of a detecting device the function of which being to detect malignant processes of a living organism; the dielectric comprises three successive layers, each one in contact with the adjacent one: a rigid transparent electrically-insulating layer (3) capable to be arranged in surfacing contact with the optically transparent electrode (4), a flexible transparent membrane (2) positioned on the free surface of the rigid transparent electrically-insulating layer (3) and a dark opaque flexible membrane (1) positioned on the free surface of the flexible transparent membrane (2), the free surface of such dark opaque membrane (1) being capable to allow contact with a part of a living organism.

An image-receiving camera (5) is mounted under the optically transparent electrode (4) [FIG. 1].

Device operation is as follows: pulses of high voltage (HV) are applied onto electrode (4) to cause gas-discharge glow around the object under examination (6) in planes of both flexible transparent membrane (2) and an opaque one (1). The light passes through both transparent dielectric (3) and electrode (4) and is then projected onto light-sensitive matrix of camera (5). Flux of light directed towards image-receiving camera passes through transparent insulating dielectric (3) to reach camera without a hindrance while the light flux directed opposite is absorbed by the dark surface of opaque membrane (1). Thus, camera (5) only records a "pure" discharge picture free of reflected light beams.

A human finger or any other object is placed onto the surface of opaque flexible membrane (1). Pulses from high voltage (HV) generator are sent to transparent electrode (4) causing both ionization and discharge of air that surrounds the exposed object, the latter being pressed to the surface of opaque membrane, while image-receiving camera captures the image and passes it to computer using image-capturing software. Gas-discharge imaging is carried out in the absence of bright ambient light (an object to be imaged is covered with a dense cloth or a special cover). A camera-activating signal also switches on high-voltage generator by means of computer program. The same software controls the entire process of imaging and converts the image into digital format whenever necessary. Subsequent processing and analysis of recorded images is done by another software upon completion of imaging session.

The device described above makes it possible to obtain information on the mode of dynamic system functioning and to evaluate the degree of synchronicity in the range of relatively high frequencies via assessment superficial emission of the system. In case malignant tumor is present in a body, some processes of high frequency tend to dominate over relatively slow ones thus altering the spectrum of superficial emission and affecting, correspondingly, gas-discharge radiation of body parts.

In particular, gas-discharge imaging of 10 human fingertips under conditions of discrete alteration of electrical field (within 1-5 kilohertz) enables to determine an approximate projection/location of those areas, where high-frequency components of superficial emission differ from background radiation of entire body. Both gradual alteration of electrical field and the procedure of video recording are controlled by computer means in such a way that time spans are maintained precisely both between switches of electric field and also between captures of frames. Precise time-control is crucial while comparing the character of a system's emission in various ranges of frequencies.

Figure 2:
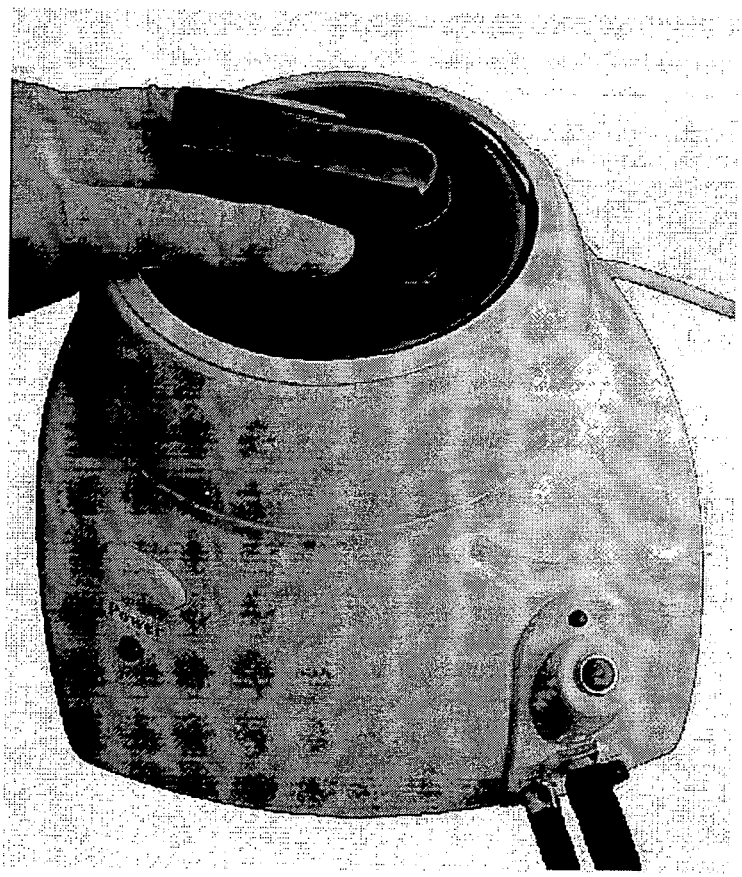

External view of the device that is nowadays used for clinical work is presented on FIG. 2. The proper position of an examinee's hand is also shown.

Figure 3:
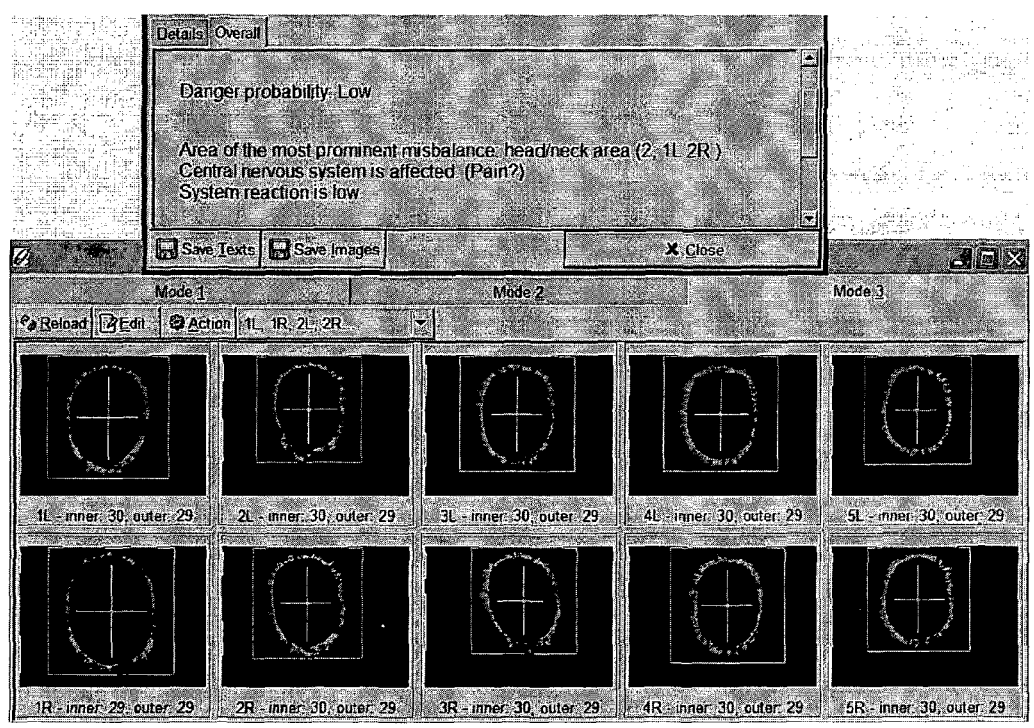

The probability of malignant (dangerous) pathology and its approximate location in the body are presently calculated using specified software that enables to display parametric data and results of their evaluation in graphic or/and text-forms. Captured images of gas-discharge glow of a person's ten fingertips are shown on FIG. 3 along with results of their evaluation.

As numerous authors have demonstrated, the intensity and character of natural or induced emission differ in malignant cells comparing to non-malignant ones [U.S. Pat. No. 5,131, 398-Method and apparatus for distinguishing cancerous tissue from benign tumor tissue, benign tissue or normal tissue using native fluorescence; Fritz-Albert Popp and Yu Yan. Delayed Fluorescence of Biological Systems in Terms of Coherent States. Physics Letters A, 293 (1-2) (2002) pp, 93-97].

Back in 2000 a new physical phenomenon (Holo-diffraction) had been discovered. The said discovery opened new possibilities of natural systems' study, since the holographic information on disordered areas present in self-organizing systems can be obtained using only minor parts of the latter (Marina Shaduri. Secondary holodiffractional radiation of biological systems. Kybernetes: The International Journal of Systems & Cybernetics. 2005 Volume: 34 Number: 5 Page: 666-680).

Subsequent experimental study of the phenomenon (conducted on humans and various animals) resulted in the determination of previously unknown functional system. Authors of the discovery —Marina Shaduri and George Chichinadze—named it Holo-Informational System (HIS). They further studied the matrix of correlation between particular disorders in human body and spectral characteristics of his/her fingertips' superficial emission. Clinical and experimental results of the study revealed significant influence of malignant pathology upon spectra of body parts' emission.

Holographic and parametric information on system disorders is obtained using 3 modes of the device operation thus enabling to evaluate gas-discharge glow in three various ranges of frequencies. Therefore, the said technique of system study was named Bioholo-tomography. Obviously, a self-organizing system when it emerges and develops within another (natural) host-system, would not function with the latter in synchronicity, since the synchronization of two individual dynamic structures implies the subordination of the less powerful organization to more powerful one. New system incorporated in another system will become a subsystem loosing its independence in case two joined organizations start to function synchronously and no competition occurs between them (System Laws and Regulations in Electrodynamics, Nature and Society. F. F. Pashchenko and I. V. Prangishvili. The Institute of Control Problems, Nauka, ISBN 5020130885).

Two asynchronously developing systems that share one and the same space, would preserve their individual features only temporarily and only in case they function with different rates. All events in newly formed and fastly developing micro-system would proceed with higher rates and frequencies thus altering integral spectrum of the macro-system where new formation is incorporated. These theoretical considerations were used as working hypothesis at the starting point of research. It became necessary to choose proper tools and technical means to obtain information on systems without any intrusion in them and also excluding any perturbation of their functioning. Living systems were chosen as objects for the said study.

Natural radiation from living systems' surfaces is too weak to be detected readily, though it might be enhanced if external electromagnetic fields of relatively high frequencies are applied to the surface of a body. To minimize the perturbation of systems' functioning only their distal and minor parts should be exposed to altered ambience. The short-term and harmless exposure of human fingertips to external electric fields (within 1-5 kilohertz), enables researchers to enhance their emission, transform it to visual glow and thus evaluate the input of body superficial emission into the discharge of ionized ambient air. The transformation of weak emission into the optic range of radiation provides readily recordable information in the form of visible glow around exposed objects, i.e., fingertips.

Known gas-discharge devices and principles of their operation do not provide reliable results while recording the emission of living objects. Correspondingly, the interpretation of non-reproducible data could not be reliable as well. The principle of living system evaluation based on gas-discharge imaging had been considered as non-valuable after numerous attempts of its usage demonstrated poor reproducibility of results.

In order to obtain stable results while detecting various, among them malignant abnormalities in living systems, the following was to be done:

It had been necessary to enhance both reproducibility and stability of gas-discharge images of biological objects, i.e., minimize influence of factors beyond control in both the surrounding media and objects under examination to final results of imaging. This result was partially attained via using additional layer of transparent [P No. 2225] membrane;

It was also crucial to improve image quality making it clearer and more contrasted through the absorption of spurious light reflected from the surface of objects under examination. This result is attained by placing an opaque membrane above a transparent layer of elastic dielectric. The usage of additional membrane while conducting gas-discharge imaging in discretely changing electric field enables to improve the reproducibility rate of results significantly;

It had been important to determine proper frequencies and intensity rates of electrical field to acquire those components of body emission, which are characteristic for malignant processes. Three different modes of electric field application were selected empirically and used for gas-discharge imaging thus making possible to evaluate high-frequency components of the emission;

It was necessary to minimize influence of the human factor to final results of the examination. In present invention all modes of operation of gas-discharge device are fully controlled and the processing/analysis of captured images are also conducted using dedicated software. While developing related software certain body of clinical and experimental work done with patients database was taken into account, since asynchronous processes of relatively high frequency are characteristic for malignant growth of tumors.

The device described above had been constructed in compliance with main requirements and standards established for medical instruments. Evaluation of its safety and measurements of some technical parameters has been conducted at Metrology Institute of Georgia by National Agency for Standards, Technical Regulations and Metrology (official documentation is enclosed).

device. The group of patients comprised 19 persons with previously determined cancer of thyroid or mammary glands, while as 16 persons were included into the control group as having no evident pathology. Cancer had been detected using such methods of standard medical examination as ultrasound, X-ray, Computer Tomography and microscopy of biopsy samples.

In the group of "Cancer" there were 2 cases of thyroid gland papillocarcinoma (stages 2 and 3), 16 cases of mammary gland cancer (stages 1-3) and a case of skin melanoma with metastases in auxiliary lymph-nodes. The said group comprised 1 man and 18 women. Age of examinees varied within the range 32-59 (mean value-48,5 y). Control group of "healthy" volunteers comprised 16 persons, among them 3 men and 13 women (mean age-47,5 y).

Bioholo-tomography examination of all 35 persons has been conducted using aforementioned gas-discharge device. In the group of persons with known diagnosis of cancer (the group of "Cancer") high probability of malignancy presence had been stated in 16 cases out of 19. Thus, 3 "false-negative" results were obtained while studying emission of patients included in this group (one case of thyroid gland carcinoma and 2 cases of mammary gland cancer were not diagnosed correctly).

TABLE 1

Some parameters of gas-discharge device evaluated by experts of Georgian Metrology Institute by National Agency for Standards, Technical Regulations and Metrology

| # | PARAMETER | VALUE | NOTES |
|---|---|---|---|
| 1 | maximal instant value of high voltage impulse amplitude, kv | 5 | |
| 2 | error of installation of instant value amplitude, % | 20 | |
| 3 | repetition rate of the bundle of damped impulses, hertz | 1000, 2000, 4000 | |
| 4 | error of installation of impulses' bundles frequency, % | 2.5 | |
| 5 | duration of one impulse in a set, micro second | 11 | |
| 6 | error of installation of one impulse duration, % | 10 | |
| 7 | duration of high voltage impulse generation, second | 3 | T Three-frequency impulse charge |
| 8 | error of installation of high voltage impulses' duration, % | 10 | |
| 9 | image resolution of CCD | 640 × 480 | |
| 10 | number of images captured per second | ≥5 | |
| 11 | alternating current of power supply, v | 100-240 | |
| 12 | frequency of power supply, hertz | 50-60 | |
| 13 | maximal current used, a | ≤1.0 | |
| 14 | duration of continuous work, h | ≥8 | |
| 15 | Functioning mode | short-term, repetitive | 10 sessions in 90 seconds |
| 16 | time of functional mode set, seconds | ≤60 | the software uploading time is not included |
| 17 | maximal temperature of machine external surface after 2 h of work, ° C. | ≤40 | temperature of environment, 25° C. |
| 18 | mass of the device, seconds | ≤2.5 | |
| 19 | overall size, mm | ≤210 × 210 × 235 | |

New principle of living systems study using aforementioned gas-discharge device in humans enables to detect malignant processes via recording fingertips' emission. To prove the efficacy of novel modality for express-detection of cancer, a "blind randomized" trial had been organized in P. A. Hertzen Research Institute of Oncology" (Moscow, Russian Federation). Results of this small-scale pilot trial (enclosed as supplementary information) demonstrated high precision of new principle-based detection of malignant processes. Concise description of the said approbation is presented below.

The trial has been arranged at the Moscow Institute of Oncology, where 35 examinees underwent the procedure of their fingertips' bioholo-tomography using aforementioned Cancer had been ruled out in 12 cases out of those 16 volunteers, who were initially considered as "healthy" examinees (control group), whereas in 4 "healthy" persons the bioholo-tomography examination revealed increased probability of malignancy presence. Additional examination of examinees whose bioholo-tomography revealed increased risk, did confirm the presence of malignant pathology in 2 persons (A case of thyroid gland cancer, stage 1 and a case of mammary gland carcinoma in situ with small areas of invasion into ducts). Only 2 cases were considered as "false-positive" so far.

Thus, the very first clinical approbation of the device detecting malignant pathology in a living system via analysis of its minor parts' superficial emission, demonstrated high percentage of its results' coincidence (88%) with data obtained while using standard medical methods. Further sophistication of present software might increase this percentage by 7-10%.

New principle of systems study that is based on the evaluation of organism's gas-discharge emission might be used as a tool for the detection of malignant pathology of any location and even at early stages of tumor development, since according to presented results of clinical trial, it enables to reveal malignant processes even in clinically "mute" cases of dangerous pathology.

One may conclude that clinical and experimental results obtained while using aforementioned device for the gas-discharge detection of asynchronous processes (in the range of relatively high frequencies) proves the correctness of theoretical considerations put in the base of present innovation. The competition of two self-organizing systems, one of them being developing within the space already occupied by another (host) system, alters the emission of entire body due to the asynchronous functioning of two individual HI-systems. Since rapidly developing micro-system emits in the range of relatively high frequencies, whereas superficial emission of parental macro-system occupies the range of relatively low frequencies, the character of gas-discharge radiation in such a conglomerate differs from the glow of a solitary system. These theoretical considerations were substantiated by experimental and clinical results thus confirming the usefulness of proposed innovation for the detection of malignant processes via assessment of body parts' gas-discharge glow.

The invention claimed is:

1. A device for the gas-discharge detection of malignant processes in living organisms, which comprises:
    an optically transparent electrode for generating an electric field,
    a dielectric, the dielectric being disposed on the optically transparent electrode and configured for electrical insulation of an object under examination, and
    a progressive-scan monochrome camera positioned below the optically transparent electrode, configured to generate continuous analog video signal to be sent to a computer for further processing;
    the dielectric comprising:
        a rigid, transparent electrically-insulating layer;
        an elastic transparent object-imaging membrane, which is positioned on top of and contacting the electrically-insulating layer;
        a dark opaque elastic membrane, disposed on and contacting the object-imaging membrane to cover the object-imaging membrane and serving to absorb spurious light reflected from the object's surface, wherein such an arrangement of rigid and elastic dielectrics is effective for acquisition of reproducible and narrower spectrum gas-discharge imagery through filtering out a majority of diagnostically irrelevant, namely cancer-nonspecific spectral components, and preserving required spectral signals in vicinity of the object under examination;
    the electrode being configured to cause ionization and discharge in air surrounding the object under examination which is positioned upon the dark opaque elastic membrane and no gas is imprisoned in the plane of the dielectric.

2. A device for the gas-discharge detection of malignant processes in living organisms, which comprises:
    an optically transparent electrode for generating an electric field,
    a dielectric, the dielectric being configured for electrical insulation of an object under examination, and
    a digital photographic camera generating discrete single images in digital presentation to be sent to a computer for further processing;
    the dielectric comprising:
        a rigid, transparent electrically-insulating layer;
        an elastic transparent object-imaging membrane, which is tightly positioned on top of and contacting the electrically-insulating layer;
        a dark opaque elastic membrane, disposed on and contacting the object-imaging membrane to cover the object-imaging membrane ne and serving to absorb spurious light reflected from the object's surface, wherein such an arrangement of rigid and elastic dielectrics is effective for acquisition of reproducible and narrower spectrum gas-discharge imagery through filtering out a majority of diagnostically irrelevant, namely cancer-nonspecific spectral components, and preserving required spectral signals in vicinity of the object under examination;
    the electrode being configured to cause ionization and discharge in air surrounding the object under examination when the object is positioned upon the dark opaque elastic membrane and no gas is imprisoned in the plane of the dielectric.

* * * * *